United States Patent [19]

Elsasser

[11] Patent Number: 5,550,264
[45] Date of Patent: Aug. 27, 1996

[54] PROCESS FOR THE REMOVAL OF DISSOLVED METALLIC CATALYST FROM ESTER PRODUCTS

[75] Inventor: A. Fred Elsasser, Cincinatti, Ohio

[73] Assignee: Henkel Corporation, Plymouth Meeting, Pa.

[21] Appl. No.: 274,593

[22] Filed: Jul. 13, 1994

[51] Int. Cl.$^6$ ........................................... C11B 3/10
[52] U.S. Cl. ................................. 554/176; 554/191
[58] Field of Search ....................... 554/176, 191

[56] References Cited

U.S. PATENT DOCUMENTS

| | | | |
|---|---|---|---|
| 1,224,291 | 5/1917 | Ellis | 554/176 |
| 3,404,011 | 10/1968 | Eolkin | 99/140 |
| 4,129,718 | 12/1978 | Muzzio | 536/4 |
| 4,137,398 | 1/1979 | Muzzio | 536/4 |
| 4,508,742 | 4/1985 | McLaughlin et al. | 426/330.4 |
| 4,895,681 | 1/1990 | Herrmann et al. | 260/410.6 |
| 5,026,548 | 6/1991 | Evans et al. | 424/195.1 |
| 5,053,169 | 10/1991 | Price | 554/176 |
| 5,169,989 | 12/1992 | Peterson et al. | 568/621 |
| 5,248,333 | 9/1993 | Worschech et al. | 106/38.24 |
| 5,281,339 | 1/1994 | Mainwaring et al. | 210/705 |

FOREIGN PATENT DOCUMENTS

| | | | |
|---|---|---|---|
| 026239 | 1/1979 | Australia | 554/176 |

OTHER PUBLICATIONS

Material Safety Data Sheet for PM5108, Manufacturer: The PQ Corporation, Valley Forge, PA.

Ralph K. Iler, "The Colloid Chemistry of Silica and Silicates", Cornell University Press, Ithaca, New York, 1955.

*Primary Examiner*—José G. Dees
*Assistant Examiner*—Deborah D. Carr
*Attorney, Agent, or Firm*—Wayne C. Jaeschke; John E. Drach; Henry E. Millson, Jr.

[57] ABSTRACT

A process for purifying crude ester containing residual metallic catalyst is described. The process comprises (a) adding to a crude ester product an amorphous silicon dioxide adsorbent capable of adsorbing dissolved metallic catalyst; (b) heating the combination at a temperature of between about 80° C. and about 130° C.; and (c) separating the ester from the adsorbent by filtration, such that residual metallic catalyst is retained on the adsorbent.

22 Claims, No Drawings

PROCESS FOR THE REMOVAL OF DISSOLVED METALLIC CATALYST FROM ESTER PRODUCTS

BACKGROUND OF THE INVENTION:

1. Field of the Invention

This invention relates a process for the removal of a dissolved metallic catalyst from a crude ester product. More specifically, the invention relates to a process for removal of residual soluble tin catalyst from the crude product in an organic ester synthesis.

2. Statement of Related Art

Organic esters and, in particular, carboxylic acid esters such as fatty acid esters, have widespread applicability in industry. For instance, they are widely used as surfactants in cleaning preparations; as base stocks for synthetic lubricants; as foam inhibitors both in the preparation of polymers (such as polyurethanes) and in the food industry for production of sugar-based products such as molasses or yeast and enzyme-based products such as beer; and in the production of phosphoric acid from mineral phosphates.

Carboxylic acid esters in general, and fatty acid esters in particular, are normally prepared in the presence of a catalyst to reduce reaction time and/or to increase the yield. For instance, insoluble tin powder or titanic acid esters have been employed as catalysts in the preparation of fatty acid esters. After such an esterification reaction is completed, it is desirable to remove the esterification catalyst, for example by simple filtration, if the catalyst is insoluble in the esterification reaction mixture.

In other instances, however, a soluble metallic catalyst, such as a tin salt, is used, which may not be completely removed simply by filtration. While it may be tried to remove these soluble compounds from the crude fatty acid ester product by distillation, such a procedure is expensive, time consuming and relatively ineffective. Moreover, distillation may be damaging to some fatty acid esters which cannot withstand the required heat, and ineffective in removing others having high boiling points.

It has also been tried to use certain absorbent materials as a post-treatment step to remove catalyst. Such known methods, too, are expensive and time consuming, and achieve unsatisfactory levels of catalyst removal.

SUMMARY OF THE INVENTION

The present invention thus relates to a process for effectively removing residual metallic catalyst from a crude ester product without damage to the product. The process comprises (a) adding to the crude ester product an effective amount of an amorphous silicon dioxide adsorbent which is capable of adsorbing metallic catalyst; (b) heating the combination resulting from (a) at a temperature of between about 80° C. and about 130° C.; and (c) separating the ester from the adsorbent by filtration such that residual metallic catalyst is retained on the adsorbent.

In preferred embodiments, the ester product is a fatty acid ester, e.g., methyl isostearate or polymethyl esters of $C18_n$ saturated n-basic acids, where n is typically about 2 to 5, and the catalyst is a tin salt, e.g., stannous oxalate or dibutyl tin diacetate. In other preferred embodiments, step (b) is performed at subatmospheric pressure and at elevated temperature, and step (c) is accomplished by filtration using Perlite as a filter aid. Preferably, the filtrate should contain less than 5 ppm of the metallic ion from the metallic catalyst. A preferred adsorbent should have a median particle size of about 11.0–16.0 vol. μm; L.O.D. of about 61% to about 70%; surface area of at least 600 $m^2$/gm, and preferably greater than 700 $m^2$/gm; mean pore diameter of about 10 nm; and bulk density of about 10 to about 40 $lb/ft^3$.

DESCRIPTION OF THE INVENTION

Other than in the claims and in the operating examples, or where otherwise indicated, all numbers expressing quantities of ingredients or reaction conditions used herein are to be understood as modified in all instances by the term "about".

The process of this invention is effective in removal of residual dissolved metallic catalyst from any type of esterification reaction such as the reaction of short chain carboxylic acids and alcohols. For example, the process according to the invention can be used to remove a soluble esterification catalyst from the reaction between pentanoic acid and ethanol in the preparation of ethyl pentanoate. It is particularly preferred, however, to employ the process according to the invention to remove dissolved catalysts in the synthesis of fatty acid esters. Exemplary fatty acid esters include but are not limited to methyl isostearate and polymethyl esters of $C18_n$ saturated n-basic acids such as dimethyl esters of a C18 saturated branched dimeric dibasic acid or the trimethyl ester of the C18 trimeric tribasic acid.

Of the latter class of esters are generally meant the reaction product of oleic acid (a monounsaturated C18 acid) with itself which forms a mixture of dimers, trimers and lower oligomers (e.g., $n \leq 5$). The mixture which results may be further refined by hydrogenation, by bleaching or by distillation, to separate out dimer or trimer, then reacted with methanol to form the polymethyl esters.

An example of a crude ester product which has been purified of tin catalyst in accordance with this invention is the dimethyl ester of C36 branched saturated dibasic acid having a maximum acid value of 1; maximum iodine value of 10; minimum saponification value of 185; flash point of 293° C.; 100° F. viscosity of 48 cSt; 210° F. viscosity of 7 cSt; 82% transmission; specific gravity of 0.9190 at 25° C.; pour point of –10° F.; and contains 94% dibasic acid and about 3% each of monobasic and polybasic acids on HPLC analysis.

Another example of a crude ester product which has been purified in accordance with this invention is methyl isostearate, prepared by reacting methanol with a mixture of isostearic acid, stannous oxalate catalyst, and carbon. The ester product has the following maximum specifications:

| | |
|---|---|
| acid value (max) | 2.0 |
| hydroxyl value (max) | 3.0 |
| iodine value | 10.0 |
| tin (ppm) (before treatment) | 300 |
| color (Gardner) | 9.0 |
| appearance | clear/dirt free |

Yet another example of a crude ester product which has been purified of a soluble catalyst in accordance with this invention is the dimethyl dimerate of a C36 acid which has been bleached for color clarity using a bleaching clay. This ester is made from oleic acid dimer, methanol and stannous oxalate. The resultant product has a maximum acid value of 1.0 and a maximum hydroxyl value of 5.0.

Still another crude ester product which has been purified of soluble catalyst in accordance with this invention is trimethyl trimerate. It is the trimerate of an oleic acid reaction product which has been enriched in trimer. The resulting ester product, again, has a maximum acid value of 1.0, a maximum hydroxyl value of 5.0 and is clear and dirt-free.

Typical dissolved metallic catalysts are, for example, salts of tin and titanium such as stannous oxalate, dibutyl tin diacetate, triisopropyl titanate, derivatives or residues of these, and mixtures of these.

A catalyst of particular interest is stannous oxalate, which, of course, results in residual tin salt which are to be removed in accordance with the invention.

While the catalysts which are to be removed in accordance with the invention are referred to herein as "metals,", "dissolved metals,", "metallic,", "metal salts," etc., it is to be generally understood that what is meant in each instance is ionic metal rather than elemental metal. Such catalysts are typically used in amounts of about 100 to about 5000 parts per million (ppm) based on the weight of starting materials. Preferably, between about 500 and about 2500 ppm of catalyst are used. It is desired that most of the metallic salt/catalyst residue is removed after esterification. Thus, the invention seeks to reduce the amount of metallic salt to less than about 20 ppm, and preferably less than about 5 ppm.

It has been found that such reduction in amount of dissolved metallic may be accomplished without the need for distillation when a particular adsorbent having a porous structure and an enormous internal surface area, and which is capable of effectively adsorbing dissolved metallic, is employed. This adsorbent is an amorphous, hydrous silicon dioxide having a median particle size of about 11.0 to about 16.0 vol. μm, and preferably about 15.0 μm; an L.O.D (i.e., loss on drying, % water loss) value of about 61.0% to about 70.0%, and a surface area of at least 600 $m^2$/gm, and preferably greater than about 700 $m^2$/gm.

The first step of the process of the invention comprises adding to a crude ester product an amorphous silicon dioxide adsorbent capable of adsorbing metallic catalyst.

A particularly preferred adsorbent is PM5108® food grade hydrous silica, also referred to as Britesorb® PM5108, from the PQ Corporation, Valley Forge, Pa., which comprises 33% amorphous silica in water; is used as an aqueous slurry; has a mean particle size of 11.0–16.0 vol. μm, an L.O.D. of 61.0–70.0%, a surface area of greater than 600$m^2$/gm, pH of 2.0–3.5, an untamped bulk density of about 16 lb/$ft^3$, and mean pore diameter of about 10 nm; and contains less than 10 ppm of heavy metallics.

The adsorbent material required by the invention is particularly effective because of its porous, sponge-like structure and controlled pore size, allowing it to act as a selective adsorbent.

The amount of adsorbent used in the process according to the invention is any amount which is effective in removing the dissolved metal catalyst from an esterification reaction. The adsorbent effective amount will, therefore, vary depending upon many factors which are peculiar to a particular esterification reaction system such as the nature of the starting acid, alcohol, esterification catalyst, the time which the adsorbent contacts the esterification reaction mixture, the specific gravity of the crude ester product being processed, the temperature, and the like. Therefore, the effective amont of adsorbent for any particular crude ester will be readily ascertainable by those of ordinary skill in the art. While the adsorbent effective amount will vary as described above, the adsorbent of the invention will typically be used at a level of from about 0.1% to about 10.0% based on the weight of the crude ester product to be treated, preferably about 0.5 to about 3.0 percent, and more preferably about 1.0 percent to about 2.0 percent.

Preferably, the adsorption step is carried out at subatmospheric pressure, e.g., about 22 to 26 inches Hg, and preferably about 25 inches Hg vacuum.

Optionally, certain additives may be used in combination with the adsorbent, which do not affect the dissolved metallic content of the final product, but which improve the process or product in other ways. For instance, a filter aid (such as Perlite from GREFCO, Inc. Torrance, Calif.) may be used to increase the rate of filtration. A bleaching clay (e.g., Attapulgus clay) may be used to improve color of the product. When used, the filter aid can either be added with the adsorbent, which is preferred, or may be used as a pre-coat on the filter. The bleaching clay, when used, is added with the adsorbent. Combination of the crude ester, optional additives, and adsorbent is effected, e.g., by simple mixing, to optimize surface contact.

In the process of the invention, after the prescribed amount of adsorbent is added to the crude ester, as a second step, the resulting combination is heated at a temperature of from about 80° C. to about 130° C., e.g., about 90° C. to about 100° C., for a period of at least about 5 to 10 minutes, and preferably about 45 to about 60 minutes.

As a third step, the ester is separated from the adsorbent by filtration, at a temperature of between about 20° C. and about 60° C., preferably between about 20° C. and about 30° C. If a particularly viscous ester is used, it may be optional to use a filtration temperature above this preferred range.

After filtration, the metallic catalyst for which removal was desired is retained on the adsorbent. The filtrate which results should thus be reduced in amount of residual metallic from catalyst to contain less than about 20 ppm, and preferably less than 5 ppm, relative to the ester. This represents a reduction in metallic salt of about 98%, preferably at least about 99.7%, based on the original weight of catalyst in the ester product.

The Examples which follow are intended as being merely illustrative of the invention. Numerous modifications and variations thereof which are within the scope of the invention as defined by the claims appended hereto will be apparent to those skilled in the art.

EXAMPLES

The following Examples are provided to further illustrate the invention. In these Examples and elsewhere throughout this application, parts and percentages are by weight unless otherwise noted, and all temperatures in degrees centigrade (°C.) unless expressly noted to be otherwise.

EXAMPLES 1 & 2

About 25.0 g of crude dimethyl dimerate having a maximum acid value of 1.0 and a maximum hydroxyl value of 5.0 and containing 320 ppm of soluble tin salt, was added to a single-neck, round bottom 100 ml flask. About 0.5 g of PM5108® amorphous silicon dioxide adsorbent from PQ Corporation, Valley Forge, Pa., were added and the flask equipped with a pot thermometer and stirrer under 25 inches Hg vacuum. The contents were heated to about 100° C. and held at that temperature for one hour. After that time, the contents were cooled and the vacuum removed. Half of the contents were filtered into a sample bottle through a Hirsch funnel and filter paper (Example I) and the other half filtered through a sintered glass funnel using Perlite 476, from GREFCO, Inc., Torrance, Calif. (Example II). In each case, less than 5 ppm of tin were detected by Inductive Coupled Plasma, Atomic Emission Spectroscopy (ICP/AES, commonly referred to as ICP).

EXAMPLE 3

About 25.0 g of the crude ester material described in Example 1, 0.5 g of PQ Corporation's PM5108® amorphous silicon dioxide adsorbent and 0.125 g of Perlite 476 were added to a 100 ml single-neck, round bottom flask equipped with a pot thermometer and magnetic stirrer under 25 inches Hg vacuum. The contents were heated to about 100° C. and maintained at this temperature for one hour, after which time the contents were cooled and filtered through a sintered glass funnel. The filtrate contained 15 ppm tin, as determined by ICP.

EXAMPLE 4

About 25.0 g of the crude material described in Example 1, 0.5 grams of PM5108® amorphous silicon dioxide adsorbent, 0.125 g of Perlite 476 and 0.125 g of Attapulgus clay were added to a single-neck flask of the type described in the previous Example and a 25 inches Hg vacuum applied. The contents were heated to 100° C. and maintained at this temperature for one hour. The contents were cooled and filtered through a sintered glass funnel (with no filter aid). The filtrate contained less than 5 ppm of tin as determined by Inductive Coupled Plasma, Atomic Emission Spectroscopy.

COMPARATIVE EXAMPLES. 1 AND 2

Samples of the crude material used in Examples 1–4 were simply filtered through paper (Comparative Example 1) and through a bed of Perlite 476 (Comparative Example 2). The filtrate in Comparative Example 1 was shown to have 320 ppm tin, and the filtrate in Comparative Example 2, 296 ppm tin, using ICP.

EXAMPLE 5

About 1.0 g of Perlite 476 and 2.0 g of PM5108® amorphous silicon dioxide adsorbent were added to about 100 g of dimethyl dimerate having a maximum acid value of 1.0 and a maximum hydroxyl value of 5.0 in a 250 ml three-neck, round bottom flask equipped with a pot thermometer and magnetic stirrer. The combination was heated to 120° C. and held at that temperature for 1 hour under 25 inches Hg vacuum, then cooled and filtered. The resultant solution was found to contain 10 ppm of tin by ICP.

EXAMPLE 6

The procedure described in the previous Example was repeated, except that 1 g of Perlite, 2 g of P5108® amorphous silicon dioxide adsorbent and 1 gram of Attapulgus clay were combined with the 100 g of the crude ester under 25 inches Hg vacuum for 1 hour at 120° C. The resultant ester solution was cooled and filtered. It was found by the ICP/EAS method to contain 18 ppm of tin.

EXAMPLE 7

A 117 g sample of crude methyl isostearate ester from Henkel Corporation, as described above, containing 275 ppm of soluble tin salt after having been treated by a prior catalyst removal post-treatment, was added to a flask equipped with a magnetic stirrer. 2 grams of the PM5108® amorphous silicon dioxide adsorbent from PQ Corporation, Valley Forge, Pa., were added and the combination stirred for one-half hour. The material filtered well and the product was crystal clear, and was shown to contain less than 5 ppm of tin on ICP analysis.

COMPARATIVE EXAMPLES 3–5

The following experiment was carried out to show optimal levels of amorphous silicon dioxide adsorbent under one set of conditions. Three samples of a crude methyl isostearate were combined with 1%, 2% and 0.5% by weight of the PM5108® amorphous silicon dioxide adsorbent (Comparative Examples 3, 4 and 5, respectively). The starting material was shown to contain 265 ppm of tin by ICP analysis, In separate 250 ml three-neck, round bottom flasks, 103.20 g of the crude ester and 1.0312 g of adsorbent (Example 3); 100.87 g crude ester and 1.9163 g of adsorbent (Example 4); and 100.06 g of ester and 0.5031 g adsorbent (Example 5) were combined. For each flask, a pot thermometer, magnetic stirrer, heating mantel and vacuum were supplied. Temperature was in each case held at 80° C. for one hour under 26 inches Hg vacuum. Each product was filtered through Whatman #1 filter paper and analyzed by ICP. The sample of Comparative Example 3 (1% adsorbent) had a dissolved tin content of 225 ppm; Comparative Example 4 (2% adsorbent), less than 20 ppm; and Comparative Example 5 (0.5%) adsorbent, 245 ppm, demonstrating that at least 2% by weight of adsorbent is required under this particular set of conditions, where contact time, temperature and other factors may not have been optimized.

EXAMPLE 8

This Example demonstrates use of the process of the invention at pilot plant scale.

To dimethyl dimerate prepared using stannous oxalate as the esterification catalyst was added 2% by weight of PM5108® amorphous silicon dioxide adsorbent. Vacuum was applied at 4 torr, and the mixture stirred at 120° C. for 1 hour. The vacuum was broken with nitrogen and the mixture filtered through a plate and frame filter. After this treatment, 18 ppm of tin were detected by atomic adsorption spectroscopy, and less than 10 ppm by ICP/AES.

While the invention has been disclosed in this patent application by reference to the details of preferred embodiments of the invention, it is to be understood that this disclosure is intended in an illustrative rather than in a limiting sense, as it is contemplated that modifications will readily occur to those skilled in the art, within the spirit of the invention and the scope of the appended claims.

What is claimed is:

1. A process for purifying crude ester containing dissolved residual metallic catalyst comprising the steps of (a) adding to said crude ester an adsorbent effective amount of an amorphous silicon dioxide adsorbent which is capable of adsorbing metallic catalyst;

(b) heating the combination resulting from (a) at a temperature of between about 80° C. and about 130° C.; and (c) separating the ester from the adsorbent by filtration wherein said metallic catalyst is retained on the adsorbent.

2. The process of claim 1 wherein the crude ester product is an organic ester.

3. The process of claim 2 wherein said organic ester is a fatty acid ester selected from the group consisting of methyl isostearate, polymethyl esters of $C18_n$ saturated n-basic acid, where n is 2 to 5, and combinations thereof.

4. The process of claim 1 wherein the amount of said adsorbent is from about 0.5 to about 3.0 percent by weight based on the weight of the crude ester product.

5. The process of claim 1 wherein the amount of adsorbent is from about 1.0 to about 2.0 percent by weight based on the weight of the crude ester product.

6. The process of claim 1 wherein step (a) further comprises addition of an additive selected from the group consisting of filter aid, bleaching clay and combinations thereof.

7. The process of claim 1 wherein step (a) is carried out at subatmospheric pressure.

8. The process of claim 6 wherein step (a) is carried out at about 25 inches Hg of vacuum.

9. The process of claim 1 wherein step (b) is carried out at a temperature of about 90° C. to about 100° C.

10. The process of claim 1 wherein step (b) is conducted for at least about 10 minutes.

11. The process of claim 10 wherein step (b) is carried out for about 45 to about 60 minutes.

12. The process of claim 1 wherein filtration step (c) is accomplished by filtration with Perlite.

13. The process of claim 1 wherein a filtrate resulting from step (c) contains less than 5 parts per million of metallic catalyst.

14. The process of claim 1 wherein said dissolved metallic catalyst is a metallic salt selected from the group consisting of tin salts, titanium salts, and mixtures thereof.

15. The process of claim 14 wherein said catalyst is a tin salt.

16. The process of claim 1 wherein said amorphous silicon dioxide adsorbent has a median particle size of about 11.0—about 16.0 vol. μm, a loss on drying of from about 61% to about 70%, a surface area of at least about 600 $m^2$/gm, a bulk density of from about 10 to about 40 lb/$ft^3$, and a mean pore diameter of about 10 nm.

17. The process of claim 16 wherein said amorphous silicon dioxide adsorbent has a mean particle size of about 15.0 μm.

18. The process of claim 16 wherein said amorphous silicon dioxide adsorbent has a surface area of at least about 700 $m^2$/gm.

19. The process of claim 16 wherein said amorphous silicon dioxide adsorbent has a bulk density of about 16 lb/$ft^3$.

20. The process of claim 2 wherein the amount of adsorbent is from about 0.5 to about 3.0 percent by weight based on the weight of the crude ester product; and said metallic catalyst is a metallic salt selected from the group consisting of tin salts, titanium salts, and mixtures thereof.

21. The process of claim 20 wherein step (a) is carried out at subatmospheric pressure; and step (b) is carried out at a temperature of about 90° C. to about 100° C. for at least about 10 minutes.

22. The process of claim 21 wherein the amount of adsorbent is from about 1.0 to about 2.0 percent by weight based on the weight of the crude ester product; step (b) is carried out for about 45 to about 60 minutes; and the amorphous silicon dioxide adsorbent has a median particle size of about 11.0—about 16.0 vol. μm, a loss of drying of from about 61% to about 70%, a surface area of at least about 600 $m^2$/gm, a bulk density of from about 10 to about 40 lb/$ft^3$, and a mean pore diameter of about 10 nm.

* * * * *